United States Patent [19]

Caboche

[11] Patent Number: 5,436,329
[45] Date of Patent: Jul. 25, 1995

[54] HYPOCARIOGENIC HYDROGENATED SACCHARIDES

[75] Inventor: Jean-Jacques Caboche, Bethune, France

[73] Assignee: Roquette Freres, Lestrem, France

[21] Appl. No.: 998,603

[22] Filed: Dec. 30, 1992

[30] Foreign Application Priority Data

Mar. 19, 1992 [FR] France ............................ 92 03314

[51] Int. Cl.$^6$ ..................... C08B 30/18; C08B 30/20; C08B 30/12
[52] U.S. Cl. ..................... 536/103; 536/123.1; 536/123.13; 435/95; 435/96; 435/99; 435/100; 435/101; 127/29; 127/38
[58] Field of Search ............... 517/54, 60; 536/122.1, 536/123.13, 103; 127/29, 38; 435/95, 96, 99, 100, 101

[56] References Cited

U.S. PATENT DOCUMENTS

| | | | |
|---|---|---|---|
| 2,436,967 | 3/1948 | Leuck | 127/29 |
| 3,766,165 | 10/1973 | Rennhard | 127/29 |
| 4,017,363 | 4/1977 | McMullen et al. | 195/31 |
| 4,206,285 | 6/1980 | Poulson et al. | 405/96 |
| 4,445,938 | 5/1984 | Verwaerde et al. | 536/1.1 |
| 4,497,846 | 2/1985 | Boursier et al. | 426/660 |
| 4,766,207 | 8/1988 | Deger et al. | 536/18.6 |
| 4,965,354 | 10/1990 | Yanaki et al. | 536/124 |
| 5,051,500 | 9/1991 | Elmore | 536/50 |

FOREIGN PATENT DOCUMENTS

| | | |
|---|---|---|
| 0171964 | 7/1985 | European Pat. Off. |
| 0368451 | 9/1989 | European Pat. Off. |
| 1-12761 | 10/1985 | Japan |
| 2-163101 | 12/1988 | Japan |
| 8502758 | 11/1984 | WIPO |

OTHER PUBLICATIONS

SIGMA Technical note n° TDFAB-1, Jun. 91.
"J. Assoc. Off. Anal. Chem" vol. 68, n° 2, 1985, p. 399.
"Starch Chemistry and Technology"—Second edition Edited by Roy L. Whistler, 1984, Academic Press Inc.

*Primary Examiner*—Marian C. Knode
*Assistant Examiner*—Francisco Prats
*Attorney, Agent, or Firm*—Larson and Taylor

[57] ABSTRACT

The invention relates to a composition containing hypocariogenic hydrogenated saccharides which can be used as sweetening composition or as texturing agent in food products and in some pharmaceutical or veterinary products. This composition is characterized in that it has a concentration of 0.1 to 80% of hydrogenated monosaccharides, a concentration of 0.1 to 96% of hydrogenated disaccharides, a concentration of 11 to 96% of hydrogenated mono- and disaccharides, a concentration of 1 to 40% of polysaccharides which are not hydrolyzed by amyloglucosidase, the balance for 100% consisting of hydrogenated oligosaccharides or polysaccharides.

28 Claims, No Drawings

HYPOCARIOGENIC HYDROGENATED SACCHARIDES

The subject of the invention is a composition containing hypocariogenic hydrogenated saccharides which can be used as sweetening composition or as texturing agent in products intended to be ingested by humans or animals, that is to say especially in food products, and in some pharmaceutical or veterinary products.

The invention also relates to a process for preparing the said composition, as well as the application of this composition in products intended to be ingested by humans or annals.

The expression "products intended to be ingested by humans or animals" is understood to mean products intended for ingestion or for oral administration, such as various foodstuffs like confectionery products, pastries, creams, drinks, jams, sauces, ice creams, prepared animal fodder, as well as pharmaceutical, veterinary, dietary or health products such as for example elixirs, cough syrups, lozenges or tablets, chewy pastes, chewing gums, pastilles, mouth washes, and toothpastes and gels.

The expression "hypocariogenic hydrogenated saccharides" is understood to mean hydrogenated saccharides which are acidified to a lesser degree by the bacteria present in the mouth than conventional sugars such as sucrose, glucose or fructose.

Such hypocariogenic hydrogenated saccharides are already known. There may be mentioned for example sorbitol, xylitol, maltitol, erythritol, lactitol, hydrogenated isomaltulose (known under the trademark PALATINIT® or more generally under the name ISOMALT), mannitol, arabitol, threitol, isomaltitol.

Syrups containing some of these various products are already marketed, such as for example sorbitol syrups, maltitol syrups containing about 50–55% maltitol, such as for example LYCASIN® 80/55 marketed by the applicant company, or maltitol syrups containing about 72–78% maltitol relative to the dry matter, such as for example MITISORB® 75/75 marketed by the applicant company or maltitol syrups sold under the trademark MALTIDEX® 100, MALTIDEX® 200, MALBIT® and FINMALT®.

However, none of the abovementioned products, or mixtures of these various products, has all of the qualities, advantages or technological properties which it might be desirable to find in a hypocariogenic sweetening composition.

Indeed, some of the abovementioned products, such as for example sorbitol, maltitol, xylitol, erythritol or mannitol, when they are used at high strengths and concentrations, have a damaging tendency to crystallise, which makes them unsuitable for use in many food, pharmaceutical or veterinary products.

Moreover, some products such as mannitol, lactitol, threitol, and hydrogenated isomaltulose do not possess a high sweetening power. This limits their applications for example in confectionery products or pharmaceutical syrups where a pronounced sweet taste is sought before everything else. This requires the addition of artificial sweeteners such as saccharin, aspartame or cyclamates and acesulfame K, which are relatively expensive products and may be unstable.

However, some products have a high sweetening power and are difficult to crystallise. This is the case for example for some maltitol syrups. Nevertheless, these syrups then have the big disadvantage of not conferring sufficient viscosity on the products in which they are used. Yet, such a viscosity is required in products such as chewy pastes, boiled sweets, nougats, pharmaceutical syrups or elixirs or toothpastes.

Some of the abovementioned hydrogenated products are moreover very hygroscopic, which can present problems especially in the manufacture of boiled sweets, the manufactured sweets then having a real tendency to regain water, and the disadvantages of sticking to the wrapping paper.

Moreover, there could be clear advantage in being able to vary the water activity in the sweetening compositions as a function of the intended subsequent uses. Yet, this possibility does not exist at the present time, even using mixtures of two or three hydrogenated products such as those mentioned above.

Finally, for some applications, it might also be desirable to be able to freely vary the boiling point of the sweetening composition, to modify its hygroscopicity or alternatively to modify, in a given direction, the glass transition temperature or the freezing point.

A very obvious demand therefore exists for the food industry and the pharmaceutical or veterinary industry to be able to have a sweetening composition
- which is hypocariogenic, and is highly stable to enzymes,
- which has a high sweetening power,
- which does not necessarily require the addition of artificial sweeteners (it being possible for this to cause unpleasant organoleptic properties or limitations in the stability to heat),
- which has good technological properties in all types of application,
- which is compatible with most ingredients used in products intended to be ingested and which can be premixed, where appropriate, with any one of them,
- whose water activity can be easily regulated according to the application envisaged,
- whose hygroscopicity, glass transition temperature, freezing point and boiling point can be varied according to the application chosen,
- which has sufficient viscosity and texture so as to confer on the finished products acceptable "mechanical" properties and texture,
- which does not require the addition of texturing additives or auxiliary products,
- which does not present risks of crystallisation in applications where such a risk would be damaging,
- or which, on the contrary, can induce limited and controlled crystallisations in some applications where a superficial microcrystallisation or granulation are intentionally sought.

However, the applicant company has had the great merit of being able to reconcile all these numerous qualities and properties, reputed incompatible up until now, by preparing and developing a new composition containing hypocariogenic hydrogenated saccharides.

The composition containing hypocariogenic hydrogenated saccharides conforming to the invention is thus characterised in that it has, the concentrations being expressed by weight relative to the dry matter of the said composition:

a concentration of 0.1 to 80%, preferably 0.1 to 75% and still more preferably 0.1 to 70% of hydrogenated monosaccharides, a concentration of 0.1 to 96%, preferably 0.2 to 94% and still more preferably 0.3 to 90% by weight of hydrogenated disaccharides, a concentration of 11 to 96%, preferably 22% to 94% and more preferably 35 to 90% by weight of hydrogenated mono- and disaccharides, a concentration of 1 to 40%, preferably 1.5 to 30% and still more preferably 3 to 26.5% by weight of polysaccharides which are not hydrolysed by amyloglucosidase in an F test (described below), the balance for 100% consisting of hydrogenated oligo- and polysaccharides.

The hydrogenated monosaccharides may be chosen from the group comprising sorbitol, mannitol, galactitol, xylitol, threitol, arabitol and erythritol.

The hydrogenated disaccharides may be chosen from the group comprising maltitol, hydrogenated maltulose, hydrogenated isomaltulose (mixture of glucopyranosido-1,6-mannitol and glucopyranosido-1,6-sorbitol), isomaltitol, lactitol, and hydrogenated inulobiose.

The hydrogenated oligosaccharides and polysaccharides may consist of maltotriitol, maltotetraitol and other hydrogenated oligo- and polysaccharides obtained by hydrolysis of starch followed by a hydrogenation. However, the said hydrogenated oligosaccharides and polysaccharides may also consist of cellobiitol, cellotriitol, xylobiitol, xylotriitol, inulotriitol and other hydrogenated oligo- and polysaccharides obtained by hydrolysis, generally acid hydrolysis, of cellulose, xylans and fructans such as for example inulin followed by hydrogenation.

In order to determine on the compositions the concentration of polysaccharides which are not hydrolysed by the enzyme amyloglucosidase, the F test is used which corresponds to the test for the determination of "total food fibres" developed by the company SIGMA Chemical Company P.O. Box 14508, St. Louis, Mo. 63178 USA and which is described in detail in the SIGMA technical note No. TDFAB-1 of June 1991.

This test consists essentially in determining the amount of material contained in the hydrolysate, which is not hydrolysed by an amyloglucosidase in the presence of a thermoresistant α-amylase and a protease. This amount is expressed in percentage relative to an amount of about 1 g of hydrolysate previously dried under vacuum at 70° C. overnight.

To carry out this test, the procedure is as follows:

1) Four samples of about 1 g of hydrolysate previously dried under vacuum and cooled in a desiccator overnight are weighed to within 0.1 mg and are introduced into a 400 ml tall-shaped beaker.
2) 50 ml of phosphate buffer (0.05M) at pH: 6.0 are added to each of the four beakers.
3) 0.05 ml of a solution of alpha-amylase (Sigma product no. A 3306) is added to each of the beakers and mixed thoroughly.
4) Each beaker is covered with an aluminium foil before being placed in a boiling water bath to incubate them for 30 min starting from the moment when the temperature in the beakers reaches 95° C. The mixture is gently stirred at regular 5 minute intervals.
5) The solutions are cooled to room temperature.
6) The pH of the solutions is adjusted to 7.5±0.1 by adding to each beaker 10 ml of 0.171N NaOH. The pH is checked and it is adjusted where appropriate with sodium hydroxide (0.171N) or phosphoric acid (0.205M).
7) 5 mg of protease powder (Sigma product No. P-3910) are added to each of the beakers.
8) The beakers are covered with an aluminium foil and they are incubated at 60° C. for 30 min, with continuous stirring. The incubation time of 30 min starts from the moment when the internal temperature of the beakers reaches 60° C.
9) The mixture is cooled to room temperature.
10) 10 ml of 0.205M $H_3PO_4$ are added to each of the beakers in order to adjust the pH to 4.5±0.2. The pH is checked. It is carefully adjusted, where appropriate, with the sodium hydroxide or phosphoric acid solutions.
11) 0.3 ml of amyloglucosidase is added (Sigma product No. A.9913) to each beaker.
12) Each of the beakers is covered with an aluminium foil and incubated for 30 minutes at 60° C., with continuous stirring. The incubation time of 30 min starts from the moment when the internal temperature of the beakers reaches 60° C.
13) 280 ml of 95% ethanol (v/v), preheated to 60° C., are added to each of the beakers. (95% ethanol v/v: 50 ml of demineralized water, pure alcohol complement to 1000 ml at 20° C.).
14) A precipitate is allowed to form by allowing the mixtures to stand at room temperature for at least 60 minutes, or overnight (the same time for each of the 4 tests).
15) The contents of each of the beakers are filtered under vacuum over a sintered glass crucible and Celite bed, and they are successively and carefully washed with:

three times 20 ml of 78% ethanol (v/v) (78% ethanol v/v: 220 ml of demineralized water, pure ethanol complement to 1000 ml at 200° C.)

two times 10 ml of 95% ethanol (v/v)

and two times 10 ml of acetone.

16) The four filters are dried overnight at 70° C. under vacuum.
17) These filters are cooled in a desiccator before being weighed to within 0.1 mg, this weight being regarded as the sum of the weight of the filtration residue (polysaccharides not hydrolysed by amyloglucosidase, plus proteins, plus ash) and the weight of the crucible with Celite.
18) The protein concentrations of two of the four filtration residues resulting from the four tests are determined by proceeding according to the Kjeldahl method, using a correction coefficient of 6.25.
19) The amounts of ash are determined on the other two filtration residues by placing the crucibles in an oven at 525° C. for 5 hours.
20) The amounts of polysaccharides not hydrolysed by amyloglucosidase are calculated for the four tests as indicated in the SIGMA technical note and a mean value is calculated for these amounts which is expressed in terms of the mean of the amounts of hydrolysate material dried overnight at 70° C. under vacuum, taking into account in the calculation, the results of the four blank tests (without dry hydrolysate) carried out in parallel.

This F test constitutes a variant of the test for the determination of total food fibres in foodstuffs described in "J. Assoc. Off. Anal. Chem." Vol 68, No. 2, 1985, p 399.

It has the advantage of being standardised, of being able to be carried out using a complete analytical kit and of being repeatable and reproducible.

The concentrations of polysaccharides which can be precipitated in ethanol and which are not hydrolysed by amyloglucosidase can also be determined on the compositions conforming to the invention using another test which has been termed test A, by carrying out the procedure as follows.

A sample of 10 g of the sweetening composition conforming to the invention, adjusted by the addition of water or by evaporation to a Brix of 75±0.2, equivalent to a refractive index of about 1.478, is used for the determination of the level of hydrogenated polysaccharides which can be precipitated in ethanol. It is recalled that Brix is a unit of measurement which is commonly used in the starch industry and that the Brix of a syrup is very easily determined by a refractometer reading. A Brix of 75 generally corresponds, for the compositions conforming to the invention, to a dry matter content approximately equal to 75%.

The sample of 10 g of the sweetening composition conforming to the invention at 75 Brix is supplemented with 30 cm$^3$ of distilled water and 60 cm$^3$ of absolute ethanol. The mixture is allowed to stand for one hour at 0° C. It is then centrifuged at 0° C. for 15 min at 10,000 g. The pellet obtained is dried in a vacuum oven maintained at 80° C. The weight of the precipitate obtained, P1, represents the weight of polysaccharides which can be precipitated in ethanol contained in the 10 g of initial sample, that is to say about 7.5 g of dry matter.

In order to determine the concentration, in the sweetening composition conforming to the invention, of hydrogenated polysaccharides which can be precipitated in ethanol and which are not hydrolysed by amyloglucosidase, an A test is used which consists in subjecting the previously obtained ethanol-precipitated polysaccharides to an enzymatic attack using a thermoresistant alphaamylase, a protease and an amyloglucosidase, then in carrying out a precipitation of the polysaccharides which are not hydrolysed with 95% ethanol, in filtering the precipitate thus obtained, in washing the latter in alcohol and acetone and finally in determining the weight, P2, of residue obtained.

This test is also described in "J. ASSOC. OF ANAL. CHEM." Vol. 68, No. 2, 1985, p. 399, article to which reference can be made.

A composition containing hypocariogenic hydrogenated saccharides conforming to the invention can be characterised in that it has, the concentrations being expressed by weight relative to the dry matter of the said composition:
- a concentration of 0.1 to 65%, preferably 0.1 to 60% and still more preferably 0.1 to 55% of hydrogenated monosaccharides,
- a concentration of 10 to 96%, preferably 15 to 94% and still more preferably 15 to 90% by weight of hydrogenated disaccharides,
- a concentration of 1 to 30%, preferably 1.5 to 25% and still more preferably 2 to 15% by weight of polysaccharides which can be precipitated in ethanol and which are not hydrolysed by amyloglucosidase in an A test described above.

It is essentially by virtue of the presence of the selected concentration of hydrogenated polysaccharides not hydrolysed by amyloglucosidase that it is possible to obtain, by concomitantly selecting on the other hand the concentration of hydrogenated mono-, di-, oligo- and polysaccharides, a sweetening composition possessing all the qualities required in most applications, such as for example the absence of crystallisation, the possibility of adjusting the viscosity, the boiling point, the glass transition temperature, the freezing point, the hygroscopicity and the sweetening power.

To prepare the sweetening composition conforming to the invention, the procedure is carried out as follows or in a similar manner.

First, a fraction comprising the polysaccharides not digested by amyloglucosidase is prepared. To do this, at least one dextrin and/or polyglucose is subjected to an enzymatic treatment comprising at least the action of a saccharifying enzyme such as amyloglucosidase or beta-amylase, the conditions for this treatment being chosen such that the DE of the dextrin and/or polyglucose hydrolysate obtained at the end of this treatment is between 5 and 80, preferably between 10 and 65, the hydrolysate obtained then being hydrogenated and then purified in a manner known per se.

The term "polyglucose" is understood to mean the products predominantly consisting of 1–6 bonds, obtained by condensation or rearrangement from glucose or from one or more sugars, which may be reduced, under the combined action of heat and acids in a medium practically devoid of water. Such polymers have been described many times and can be obtained by processes such as those described especially in U.S. Pat. Nos. 2,436,967, 3,766,165, 4,965,354, 5,051,500, JP 01-12761 and JP 02-163101. Advantageously, these polymers are obtained from glucose and citric acid, optionally in the presence of sorbitol.

Within the scope of the present invention, the term "dextrin" is understood to mean the products obtained by heating starch adjusted to a low moisture level, generally in the presence of acidic or basic catalysts. This "dry roasting" of starch, most commonly in the presence of an acid, results both in a depolymerisation of the starch and a condensation of the starch fragments obtained, and leads to the production of highly branched molecules. Dextrins are part of the oldest starch derivatives and their preparation, their applications, the various types of dextrins as well as their properties are described for example in the book entitled "Starch Chemistry and Technology"—Second Edition—Edited by Roy L. WHISTLER—1984—Academic Press Inc.

Enzymatic treatments of dextrin have already been proposed in the literature as for example in European Patent Applications No. 0368451 or JP-A-62091501, but for other purposes. These prior art documents will be more fully analysed later.

Preferably, the dextrins obtained by the dry roasting of starch in the presence of an acidic catalyst such as hydrochloric acid, are used for the preparation of the compositions conforming to the invention. The acid is thus sprayed on the starch and the mixture obtained is predried, for example from 80° to 130° C. until a water content of less than or equal to about 5% is obtained. Then the mixture is "roasted" at a temperature of about 140° to 250° C. for a period of 30 minutes to about 6 hours in order to obtain the dextrin, which has at the end of the reaction a DE of about 0.5 to 10. Any type of starch, and especially maize starch, potato starch, wheat starch, cassava starch, rice starch or pea starch can be used for the preparation of these dextrins.

According to the ISO 1227 standard of 1979, a dextrin is obtained from starch or starch flour converted by heating in the dry state with or without the addition of small amounts of chemical reagents. Traditionally, dextrins are classified into two categories: white dextrins whose appearance is not very different from that of the raw material used, and yellow dextrins, which are produced under more drastic conditions and whose depth of colour can be correlated with the degree of modification of the native structure. The four types of reaction occurring during the dextrinisation are, at low temperatures, essentially hydrolysis of the alpha 1-4 bonds and then, at the higher temperatures, condensation, transglycosidation and anhydrisation reactions.

Dextrins such as those marketed by the applicant company under the trademarks TACKIDEX DF 165, TACKIDEX DF 155, TACKIDEX JO 55 K can be advantageously used.

The dextrin, polyglucose or mixture of dextrins and/or polyglucoses selected are thus suspended in water at a dry matter content of about 20 to 70%, preferably 20 to 45% in order to undergo saccharification using at least one saccharifying enzyme consisting of amyloglucosidase and/or beta-amylase.

Preferably, and although this is not necessary in all cases, this enzymatic action of beta-amylase and/or amyloglucosidase may be preceded by the action of an alpha-amylase which is preferably thermoresistant.

Likewise, the saccharification treatment can be followed or accompanied by the action of an alpha-amylase.

According to a preferred mode, a treatment using an enzyme which hydrolyses the 1-6 bonds of amylopectin, such as for example isoamylase or pullulanase, can also be used. This treatment, using an enzyme which hydrolyses the 1-6 bonds of amylopectin, which may precede, accompany or follow the saccharification treatment, is particularly advantageous insofar as the action of this enzyme makes it possible to allow only the polysaccharides which are very difficult to digest enzymatically, to remain in the dextrin and/or polyglucose hydrolysate obtained.

The enzymatic action of amyloglucosidase, beta-amylase and, optionally, alpha-amylase, pullulanase or isoamylase, on dextrin, polyglucose or on their mixture, makes it possible to obtain a fraction comprising, in addition to glucose, maltose, maltotriose and other oligosaccharides and polysaccharides, polysaccharides which are not digested by amyloglucosidase.

This fraction may be directly hydrogenated or subjected to an additional treatment in order to enrich it with polysaccharides which are not digested by amyloglucosidase. Such a treatment may consist for example of a membrane procedure such as reverse osmosis or ultrafiltration, solvent precipitation or chromatographic fractionation. If desired, it is even possible to go as far as practically isolating the said polysaccharides, preferably by chromatographic fractionation on cationic resins in alkali metal or alkaline-earth metal form or on zeolites.

This chromatographic fractionation can therefore be carried out before hydrogenation and it is then quite obviously necessary to subsequently hydrogenate the polysaccharides not digested by amyloglucosidase. But in conformity with a preferred embodiment of the invention, this chromatographic enrichment or separation treatment of the polysaccharides is carried out after hydrogenation. This thus makes it possible to use only one hydrogenation treatment for preparing the composition containing hydrogenated saccharides conforming to the invention, and, moreover, the separation of the polysaccharides is more effective in this case.

Having therefore thus obtained a fraction containing optionally hydrogenated polysaccharides which are not hydrolysed by amyloglucosidase, the sweetening composition conforming to the invention is then prepared.

For this, starting with a defined percentage of this composition, this percentage quite obviously depending on the concentration of polysaccharides in the said fraction, optionally hydrogenated monosaccharides, disaccharides, oligosaccharides and polysaccharides are then added in defined proportions for each of these groups of constituents.

According to a first variant, there are added to the non-hydrogenated polysaccharide fraction obtained at the end of the enzymatic treatment of dextrin, polyglucose or a mixture thereof, optionally followed by a chromatographic enrichment or fractionation step, non-hydrogenated monosaccharides, disaccharides or oligosaccharides and polysaccharides in defined proportions for each of these various constituents. And the composition thus obtained is hydrogenated.

According to a second variant, which is preferred, the polysaccharide fraction is separately hydrogenated and monosaccharides or disaccharides or oligosaccharides and polysaccharides already hydrogenated are added thereto in defined proportions for each of these various constituents.

By way of example, a sweetening composition conforming to the invention can thus be prepared by mixing an inulin hydrolysate, birchwood or maize cobs, a starch hydrolysate and a fraction containing the polysaccharides obtained by enzymatic hydrolysis of a dextrin and/or a polyglucose, these hydrolysates and this fraction being mixed in predefined proportions, and the mixture thus obtained is then hydrogenated.

The sweetening composition prepared under these conditions contains at the same time xylitol, arabitol, sorbitol, mannitol, maltitol as well as hydrogenated polysaccharides which are not digested by amyloglucosidase.

As already mentioned above, processes consisting in enzymatically hydrolysing a dextrin have already been proposed in the literature.

Thus, European Patent Application No. 0368451 describes a process essentially consisting in dissolving a pyrodextrin in water and in reacting an alpha-amylase with the resulting solution. This process is designed to remove the undesirable odour and taste from pyrodextrin and to give dextrins containing dietary fibres.

Thus, according to the process described in this patent application, a pyrodextrin is dissolved in water and then hydrolysed using alpha-amylase. However, other enzymes may be added after the alpha-amylase treatment: this applies to transglucosidase, beta-amylase and glucoamylase. The product obtained at the end of this enzymatic treatment can then be hydrogenated. Monosaccharides and oligosaccharides may be added to the initial starch intended to be dextrinised, in order to increase the concentration of indigestible dextrin in the final product.

The object of the abovementioned patent application is therefore essentially to provide a product which is not very digestible, "low in calorie", which acts as dietary food fibre and which essentially consists of polysaccharides which are not very digestible. The content of the product exemplified by "indigestible dextrins" thus ranges between about 27% and about 95% and the concentration, in these products, of polysaccharides whose degree of polymerisation is equal to or greater than 4, is between about 60% and about 92% by weight.

Another process for producing dietary food fibres from dextrins has, moreover, been described in Japanese Patent Application JP-62091501. This process consists in treating, at a high temperature, a hydrogenated starch hydrolysate by carrying out this heating under anhydrous conditions at 150°-250° C. in the presence of a catalyst consisting of an inorganic acid or an organic acid.

Just like the patent application mentioned above, this document therefore relates to the production of products which are not very digestible in the body, so-called "low in calories" and which act in the body as food fibres. Their object is therefore far removed from the object of the present invention, which is to prepare a sweetening product consisting of hydrogenated saccharides with a high sweetening power, which is hypocariogenic and has technological properties which can be used both in sweets, chewing gums and toothpastes, and in drinks and pharmaceutical or veterinary elixirs, or other products.

Moreover, it may be emphasised that the said prior art documents do not describe or suggest a use of enzymes which hydrolyse the 1-6 bonds of amylopectin, enzymes whose expected action within the scope of the present invention makes it possible to produce a fraction containing hydrogenated polysaccharides with a very low digestibility, which constitutes quite a significant advantage.

Preferably, the amounts and conditions for the action of the various enzymes used for preparing the fraction obtained by enzymatic hydrolysis of dextrin and/or polyglucose, of dextrins or of polyglucoses, and intended for the preparation of the hypocariogenic sweetening composition conforming to the invention, are chosen from the following:

amyloglucosidase: 4,000 to 500,000 international units/kg of dry substrate, a temperature of 50° C. to 60° C., duration of action from 30 to 100 hours, a pH of 5.0 to 6.0, beta-amylase: 100 to 10,000 LINTNER units per kilogram of dry substrate, a temperature of 50° C. to 60° C., duration of action from 30 to 100 hours, a pH of 5.0 to 6.0, alpha-amylase: 20 to 2,000 KNU units (Kilo Novo Units) per kilogram of dry substrate, a pH of 5.0 to 6.0, a temperature of 50° C. to 60° C., duration of action from 16 to 100 hours, enzyme hydrolysing the 1-6 bonds : 150 to 15,000 ABM units (ABM, CHESHIRE, ENGLAND) per kilogram of dry substrate, optionally in the presence of 50 to 100 international units of beta-amylase per kilogram of dry substrate, a pH of 5.0 to 6.0, a temperature of 50° C. to 60° C., duration of action from 24 to 100 hours.

The enzymes used may be:
in the case of amyloglucosidase, fungal amyloglucosidases,
in the case of beta-amylase, microbial or plant beta-amylases,
in the case of alpha-amylase, bacterial or fungal alpha-amylases,
in the case of enzymes hydrolysing the 1-6 bonds, those chosen from pullulanase and isoamylase such as for example: PULLUZYME 750L from ABM or CK20L from AMANO.

Within the scope of the present invention, the hydrogenation of the hydrolysate obtained following the enzymatic hydrolysis of dextrin, of polyglucose or of the mixture of dextrins and/or polyglucoses, optionally comprising additional saccharides, oligosaccharides and polysaccharides, may be carried out in a manner known per se, by hydrogenation over RANEY nickel or by hydrogenation over noble metals.

This hydrogenation is carried out after purification of the hydrolysate, for example by a treatment over activated carbon, after demineralisation over cationic and anionic resins. The hydrogenation may be carried out for example over a RANEY nickel catalyst, at a temperature of 130° C. and at a hydrogen pressure of 50 bars.

After hydrogenation, the syrup obtained is filtered and then demineralised, and then concentrated until the concentration at which it is marketed is obtained, which is generally between about 70 and 85 Brix, equivalent to about 70% to 85% of dry matter. It may also be dried for example by spray-drying.

The hydrogenation is generally carried out until there is obtained a percentage ratio of residual reducing sugars to dry matter of less than 0.50, preferably less than 0.25 and still more preferably less than 0.20.

One of the essential characteristics of the sweetening composition according to the invention lies in its hypocariogenicity, that is to say in its capacity to cause a much lower acidification by the bacteria present in the mouth, than conventional ordinary sugars such as glucose, fructose, sucrose or glucose syrups.

According to a completely advantageous embodiment of the invention, the sweetening composition conforming to the invention has the property of being able to be described as non-cariogenic according to a B test.

This B test had been developed by the applicant company in order to monitor the non-cariogenic character of the hydrogenated hydrolysates marketed from 1978 under the name LYCASIN ® 80/55. This simple test is based on the determination in vitro of the acidification of a given amount of hydrogenated starch hydrolysate after inoculating the medium with saliva. It is based on the determination of the drop in pH over time for a culture broth containing the test product, after then inoculating with saliva obtained from several donors, in comparison with a control culture broth not containing any carbohydrate. It should be emphasised that this test is not adequate for an absolute characterisation of the non-cariogenicity of a product since its results can vary for example with the quality of the saliva used, but it makes it possible nevertheless to establish valid comparisons between the various products.

The detailed procedure for this test is as follows.

A series of tubes are prepared containing 10 ml of a sugar-free nutrient culture medium (trypticase medium containing 2% dry matter), at p 7, and these tubes are sterilised by transferring to an autoclave at 120° C. for 20 minutes.

In a first series of five tubes, 1 ml of sterile water is introduced in order to prepare a control series.

In a second series of five tubes, 1 ml of an 18% (w/v) solution of the test product is introduced.

Then the five tubes for each series are inoculated with the same volume of 0.2 ml per tube of a dilution of human saliva collected from 5 donors.

The formation of acids is then monitored by measuring the pH, a first measurement being carried out before incubation and the other measurements being carried out after incubations, at 30° C. of 3, 6, 13, 18 and 21 hours respectively.

For a product to be considered as non-cariogenic based on this B test, the difference in pH observed between the control after 21 hours and the test product after 21 hours must not be too pronounced and, in practice, must not be more than 1 unit of pH.

One of the great advantages of the present invention is that it provides sweetening compositions which possess the property of being non-cariogenic based on this B test, while nevertheless containing a substantial amount of hydrogenated oligosaccharides and polysaccharides.

Other advantages of the present invention are to provide sweetening compositions which are stable and which can be used as sweetening agent and as texturing agent in products intended to be ingested by humans and animals, these products possessing a liquid or viscous, pasty, jelly-like or solid texture, which are completely compatible with the other ingredients used in these products and which can be optionally premixed, without any drawback, with a preservative, an emulsifier, a flavouring, a sugar, a polyol, an intense sweetening agent, an acid, a pharmaceutical or veterinary ingredient, a fat, an inorganic or organic filler such as polydextroses, fibres, fructooligosaccharides, gums, an organic or inorganic gelling agent such as proteins, pectins, modified celluloses, algae and seed extracts, bacterial polysaccharides and silicas.

These products, which are intended to be ingested by humans or animals, may possess a liquid or viscous texture, such as drinks, syrups, emulsions, suspensions, elixirs, mouth washes, ampoules with contents to be taken orally; a pasty texture, such as non crystallised or semi-crystallised confectionery products such as hard sweets, jellies, gums, chewy pastes, caramels, chewing gums, fodders, and cereal bars; a jelly-like texture, such as food gels, such as custard tarts, jams, jellies, milk desserts or pharmaceutical and veterinary gels, toothpastes; a solid texture such as pastry, biscuit and bakery products, tablets, side dishes, spray-dried or extruded sweetening or flavouring powders, and pharmaceutical or veterinary freeze-dried products.

Another advantage of the composition containing hydrogenated saccharides according to the invention is being particularly stable to microbial enzymes and to oxidising or reducing chemical reagents.

This advantage can be exploited in the formulation and preparation of products which are not intended to be ingested by humans and animals, such as for example cosmetic products, plastics, metal quenching, skin treatment, and casting moulds.

The examples below, which are given with no limitation being implied, will illustrate the invention more clearly.

EXAMPLE 1

Into a 25-liter tank, stirred and thermostatted, were introduced 20 liters of a syrup prepared by dissolving in water the yellow dextrin TACKIDEX DF 165 to a dry matter content of 35%.

The pH was adjusted to 5.5 using concentrated sodium hydroxide and the tank was thermostatted at 55° C. before adding thereto:
  0.015% of the beta-amylase SPEZYME DBA, from the company GENENCOR,
  0.2% of the pullulanase PULLUZYME 750 L from the company ABM.

After 48 hours of saccharification, 0.1% of the alpha-amylase MAXAMYL HT 3000, from the company GISTBROCADES was added. The saccharification was stopped after 88 hours.

This syrup was then treated with 0.8% (volume/volume) of a solution of $H_2O_2$ at 35% (v/v) for 24 hours, at 70° C. and pH 9.5. Residual hydrogen peroxide was decomposed by adding a small amount of catalase and then the syrup was deoxygenated under vacuum before being treated with activated carbon and then demineralised on a bed of mixed resins.

The syrup was then concentrated to a dry matter content of 40% and was then hydrogenated using 5% RANEY nickel catalyst, at a temperature of 130° C. and at a hydrogen pressure of 50 bars. The hydrogenation was continued until a reducing sugar level of less than 0.5% was obtained.

Composition A

Part of this syrup conforming to the invention, called in what follows "base syrup" assaying 15.3% of maltitol, 22.4% of polysaccharides with an DP equal to or greater than 20, and 16.2% of polysaccharides which are not hydrolysed by amyloglucosidase according to the F test, was then supplemented with crystallised maltitol in a proportion such that the added maltitol represents 40% of the dry matter content of the total composition to give the composition A containing hydrogenated saccharides according to the invention.

Composition B

Another portion of this base syrup was supplemented with crystallised xylitol in a proportion such that the added xylitol represents 60% of the dry matter content of the total composition to give the composition B containing hydrogenated saccharides according to the invention.

The compositions A and B containing hydrogenated saccharides according to the invention were then concentrated to a dry matter content of 75%.

These compositions gave the following carbohydrate spectra, in addition to which the results obtained in the F test and the A test are presented (Table I).

TABLE I

|  | Composition A | Composition B |
|---|---|---|
| Dry matter % | 75 | 75 |
| Reducing sugars (% over DM) | 0.24 | 0.20 |
| DP 1 sorbitol | 2.5 | 1.7 |
| DP 1 xylitol | 0 | 60 |
| DP 2 maltitol and isomaltitol | 48.9 | 6.1 |
| DP 3 | 4.4 | 2.6 |
| DP 4 | 2.5 | 1.8 |
| DP 5 | 3.0 | 1.9 |
| DP 6 | 2.5 | 1.9 |
| DP 7 | 2.7 | 1.8 |
| DP 8 | 2.6 | 1.4 |
| DP 9–20 | 15.5 | 11.1 |
| DP > 20 | 13.8 | 9.0 |
| Polysaccharides not hydrolysed by amyloglucosidase in % (F test) | 8.7 | 5.7 |
| Precipitate P1 in ethanol (%) (A test) | 23 | 15.3 |
| Precipitate P2 (in %) after enzymatic digestion (A test) | 4.6 | 3.1 |
| Viscosity at 20° C. (cps) | 7000 | 3200 |

A cariogenicity test according to the B test was carried out on the compositions A and B. The drop in pH between the control and the compositions A and B analysed was 0.90 and 0.80 respectively. The compositions A and B are not cariogenic according to the B test.

EXAMPLE NO. 2

Another base syrup was prepared by carrying out the procedure as described below:

In a 25-liter tank, stirred and thermostatted, were introduced 20 liters of a syrup prepared by dissolving in water the yellow dextrin TACKIDEX DF 165 to a dry matter content of 35%.

The pH was adjusted to 5.5 and the temperature to 55° C. 0.05% of the amyloglucosidase OPTIDEX C 300, from the company MILES, was added per kg of dextrin and 0.1% of the alpha-amylase MAXAMYL HT 3000, from the company GIST-BROCADES, and then the saccharification was allowed to proceed for 60 hours.

The syrup obtained was treated with hydrogen peroxide as described in Example 1, before being treated over activated carbon and then demineralised over a bed of mixed resins. The mixture was then concentrated to a dry matter content of 50%. This syrup contained 45% of real glucose and 55% of oligo- and polysaccharides.

This syrup was fractionated by chromatography on a column containing a strong cationic resin, crosslinked with divinylbenzene and converted to the sodium form, and having a particle size of between 0.2 and 0.4 mm: the resin C204, marketed by DUOLITE. The fractionation was carried out for successive loadings of 0.15 liter of syrup for a column 2 meters high, containing 1.50 liter of resin. The elution of each loading was carried out using water at 60° C., at a flow rate of 0.85 liter/hour.

Each eluate loading was fractionated into two portions, one corresponding to the beginning of the elution and containing the polysaccharides, the other corresponding to the end of the elution and containing essentially glucose.

The eluates corresponding to the polysacchariderich fractions were evaporated and then reconcentrated to give a polysaccharide syrup whose carbohydrate spectrum, determined by high performance liquid chromatography, is presented in Table II.

TABLE II

| | |
|---|---|
| DP 1 (glucose) | 0.4% |
| DP 2 (maltose, isomaltose) | 0.8% |
| DP 3 (maltotriose) | 2.5% |
| DP 4 (maltotetraose) | 4.0% |
| DP 5 | 5.4% |
| DP 6 | 4.7% |
| DP 7 | 3.9% |
| DP 8 | 4.2% |
| DP 9-20 | 31.6% |
| DP > 20 | 42.6% |

This syrup, called in what follows polysaccharide syrup, was used as base to prepare the following compositions C and D according to the invention.

Composition C

Crystallised xylose was dissolved in the polysaccharide syrup so as to represent 50% of the dry matter content of the total composition, and then the resulting syrup was hydrogenated, purified and concentrated in a conventional manner.

Composition D

Crystallised xylose was dissolved in the same polysaccharide syrup so as to represent 66% of the dry matter content, then the resulting syrup was hydrogenated, purified and concentrated in the same conventional manner.

Syrups were thus obtained, whose composition relative to the drymatter content, is presented in Table III.

TABLE III

| | Composition C | Composition D |
|---|---|---|
| Dry matter % | 75 | 75 |
| Hydrogenated monosaccharides (xylitol + sorbitol) | 50.2 | 66.1 |
| Maltitol-isomaltitol | 0.4 | 0.3 |
| DP 3 | 1.25 | 0.8 |
| DP 4 | 2 | 1.5 |
| DP 5 | 2.7 | 1.8 |
| DP 6 | 2.35 | 1.6 |
| DP 7 | 1.95 | 1.3 |
| DP 8 | 2.1 | 1.4 |
| DP 9-20 | 15.8 | 10.5 |
| DP > 20 | 21.3 | 14.2 |
| Non-hydrolysable polysaccharides in % (F test) | 23.2 | 15.8 |
| Precipitate P1 (%) (A test) | 28.1 | 18.7 |
| Precipitate P2 (%) (A test) | 21.6 | 14.4 |
| Viscosity (cps) | 5900 | 4800 |

EXAMPLE NO. 3

The polysaccharide syrup obtained according to Example 2, and whose composition is given in Table II, was used, mixed with the crystallised isomaltulose marketed by the company MITSUI, in order to prepare mixtures containing respectively:

35% of isomaltulose (on a dry basis)
50% of isomaltulose (on a dry basis)
66% of isomaltulose (on a dry basis)

and these syrups were hydrogenated, purified and concentrated in order to obtain the compositions E, F and G according to the invention and having the carbohydrate spectra (expressed in % relative to the dry matter content) presented in table IV.

TABLE IV

| | COMPOSITION E | COMPOSITION F | COMPOSITION G |
|---|---|---|---|
| Dry matter content in % | 75 | 75 | 75 |
| Hydrogenated monosaccharides (sorbitol) | 0.3 | 0.2 | 0.1 |
| Hydrogenated disaccharides | | | |
| maltitol | 0.5 | 0.4 | 0.3 |
| isomaltitol | 16.5 | 25 | 33 |
| glucopyranosido-1,6-mannitol | 16.5 | 25 | 33 |
| DP 3 | 1.7 | 1.25 | 0.8 |
| DP 4 | 2.7 | 2 | 1.5 |
| DP 5 | 3.6 | 2.7 | 1.8 |
| DP 6 | 3.1 | 2.35 | 1.6 |
| DP 7 | 2.6 | 1.95 | 1.3 |
| DP 8 | 2.8 | 2.1 | 1.4 |
| DP 9-20 | 21.0 | 15.8 | 10.5 |
| DP > 20 | 28.4 | 21.3 | 14.2 |
| Non hydrolysable polysaccharides (%) (F test) | 30.0 | 23.1 | 15.9 |
| Precipitate P1 (%) (A test) | 37.4 | 28.1 | 18.7 |
| Precipitate P2 (%) (A test) | 28.8 | 21.6 | 14.4 |
| Viscosity (in cps) at 75% of DM 20° C. | 44,600 | 10,000 | 7,300 |

EXAMPLE NO. 4

In a 25-liter tank, stirred and thermostatted, are introduced 20 liters of a syrup prepared by dissolving in water, to a dry matter content of 35%, the yellow dextrin TACKIDEX DF 165 marketed by the applicant company. The pH of this syrup is adjusted to 5.5 and the temperature to 55° C., and then the following are introduced:

0.15% (w/dry w) of the β-amylase Spezyme DBA from the company GENENCOR, and 0.2% (w/dry w) of the pullulanase Pulluzyme 750 L from the company ABM.

After 86 hours, the mixture is acidified to pH 3.5 and the tank is heated to 80° C. for 20 minutes in order to inhibit the enzymes.

This syrup is filtered and then demineralised over strong cationic and weak anionic resins and adjusted to a dry matter of 40%.

This hydrolysate is then hydrogenated. For that, 5% of Raney nickel catalyst is added relative to the syrup. The hydrogenation is carried out at a temperature of 130° C., at a hydrogen pressure of 50 bars. It is continued until a reducing sugar level of less than 0.5% is obtained.

The hydrogenated hydrolysate is then purified and concentrated to 70% dry matter content. It contains about, on dry matter:
- 1% of sorbitol,
- 22% of maltitol and isomaltitol,
- 25% of polysaccharides which are not hydrolysed according to the F test.

This syrup conforming to the invention, called in what follows hydrogenated syrup S, was used as base to prepare the compositions H, I and J according to the invention.

Composition H

A portion of the hydrogenated syrup S is diluted to 60% dry matter content.

Mannitol F, marketed by the applicant company, is added to this diluted hydrogenated syrup S, in a proportion such that the mannitol represents 25% of the dry matter content of the total composition. The mixture is stirred until the mannitol is completely dissolved, and then concentrated to 70% dry matter content to give the composition H.

Composition I

In a 25-liter tank, stirred and thermostatted at 60° C., the following are introduced:

4 kg of hydrogenated syrup S,
16 kg of the sorbitol syrup NEOSORB ® 70/70 marketed by the applicant company.

The composition I was thus obtained after mixing thoroughly.

Composition J

Into a 25-liter tank, stirred and thermostatted at 65° C., are introduced:

10 kg of hydrogenated syrup S,
10 kg of the polyol syrup POLYSORB ® 70/12/12 marketed by the applicant.

These compositions gave the following carbohydrate spectra (Table V)

TABLE V

|  | COMPOSITION H | COMPOSITION I | COMPOSITION J |
|---|---|---|---|
| Dry matter content in % | 70 | 70 | 70 |
| Monosaccharides in % |  |  |  |
| Sorbitol | 0.8 | 60.3 | 8.0 |
| Mannitol | 25.2 | 5.8 | 0.5 |
| Disaccharides in % | 16.5 | 14.3 | 16.9 |
| Non hydrolysable polysaccharides in % (F test) | 16.9 | 4.6 | 11.4 |

The compositions H and I are non-cariogenic based on the B test. The composition J may be considered as hypocariogenic.

The composition H was found to be very useful for preparing sugar-free boiled sugars which are not very hygroscopic.

The composition I gave good results in the production of toothpastes, conferring on the latter, combined with silicas, an excellent jelly-like texture.

Finally, the composition J was used in the preparation of silicated casting moulds. It is a good binding and cohesion-promoting agent.

EXAMPLE NO. 5

Preparation of non-cariogenic chewy pastes comprising four compositions according to the invention.

The compositions A, B, C and D obtained according to Examples No. 1 and 2 are used to formulate non-cariogenic chewy pastes.

A control chewy paste is prepared using a mixture of crystallised xylitol and the syrup LYCASIN ® 80/55. The four recipes thus possess similar xylitol concentrations.

The recipes (in grams) before boiling the chewy pastes are given in Table VI.

TABLE VI

|  | RECIPE 1 with compositions A and B | RECIPE 2 with composition C | RECIPE 3 with composition D | RECIPE 4 (CONTROL) |
|---|---|---|---|---|
| Polyols: |  |  |  |  |
| Composition A | 732.1 |  |  |  |
| Composition B | 204.5 |  |  |  |
| Composition C |  | 245.3 |  |  |
| Composition D |  |  | 186.7 |  |
| Lycasin 80/55 |  | 691.3 | 749.9 | 844.6 |
| Crystallised xylitol |  |  |  | 92.0 |
| Hydrogenated copra | 39.5 | 39.5 | 39.5 | 39.5 |
| Gelatin solution | 20.0 | 20.0 | 20.0 | 20.0 |
| Glycerol monostearate | 3.9 | 3.9 | 3.9 | 3.9 |

TABLE VI-continued

|  | RECIPE 1 with compositions A and B | RECIPE 2 with composition C | RECIPE 3 with composition D | RECIPE 4 (CONTROL) |
|---|---|---|---|---|
| Ratio $\frac{\text{P in \% (1)}}{\text{Polyols in \% (2)}} \times 100$ | 4.3 | 5.6 | 2.9 | 0 |

(1) P in %: polysaccharides which can be precipitated in alcohol and which are not hydrolysed based on the A test for the mixture of polyols used.

(2) Polyols in %: amount of polyols present in the mixture of polyols used.

To produce the chewy pastes, the mixture of polyols is boiled at a defined temperature (130° C. or 145° C.), at atmospheric pressure; the mixture is allowed to cool to 110° C., the fat, emulsifier and gelatin solution are incorporated and then the pastes obtained are stretched before shaping and cutting them.

The rheological characteristics of the chewy pastes obtained are given in Table VII below:

TABLE VII

| BOILING TEMPERATURE °C. | RECIPE 1 | RECIPE 2 | RECIPE 3 | RECIPE 4 |
|---|---|---|---|---|
| 130° C. | Paste: correct texture not very sticky good machinability correct strength | Paste: soft slightly sticky difficult to shape incorrect strength | Paste: correct texture very slightly sticky good machinability correct strength | Paste: very soft very sticky impossible to shape no strength |
| 145° C. | Paste: firm texture non sticky good machinability correct strength | Paste: rather brittle texture non sticky good machinability correct strength | Paste: correct texture very slightly sticky good machinability correct strength | Paste: soft very sticky difficult to shape correct strength |

It can be observed that compared with the possibilities offered in the prior art, the compositions A, B, C and D make it possible to prepare xylitol-containing non-cariogenic chewy pastes, with a texture suitable for machine processing and having the correct strength during storage.

EXAMPLE NO. 6

Preparation of hypocariogenic boiled sweets comprising compositions according to the invention.

The compositions F and G obtained according to Example 3 are used to prepare boiled sweets. For that, these two compositions with a dry matter content of 75%, are dehydrated by boiling using a naked flame, and at atmospheric pressure, at the temperatures of 140° C., 145° C., 150° C. and 160° C.

Control boiled sweets are obtained by boiling ISOMALT ® (equimolar mixture of isomaltitol and glucopyranosido-1,6-mannitol) at the same temperatures.

After boiling, sweets are obtained whose water contents were found to be as follows:

TABLE VIII

| TEMPERATURE FOR BOILING | COMPOSITION F WATER % | COMPOSITION G WATER % | ISOMALT WATER % |
|---|---|---|---|
| 140° C. | 3.6 | 4.0 | 6.5 |
| 145° C. | 2.5 | 3.1 | 5.0 |
| 150° C. | 2.1 | 2.4 | 4.5 |
| 160° C. | 1.3 | 2.0 | 3.1 |

It is observed that dehydration of the compositions F and G according to the invention is easier than that of the ISOMALT syrup. Boiling the compositions according to the invention requires less energy, and they make it possible to obtain sweets having, like in the case of traditional sweets obtained with sugar, a water content of between 2 and 3%, which is necessary to endow the sweets with good stability despite the low boiling temperatures. Furthermore, the sweets obtained are hypocariogenic.

I claim:

1. A composition of hydrogenated saccharides comprising, the concentrations being expressed by weight relative to the dry matter of the composition:
   0.1 to 80% of hydrogenated monosaccharides,
   0.1 to 96% of hydrogenated disaccharides,
   11 to 96% of hydrogenated mono- and disaccharides,
   1 to 40% of polysaccharides which are not hydrolyzed by amyloglucosidase in an F test said polysaccharides being obtained by enzymatic hydrolysis of dextrin or polyglucose, said polyglucose predominantly consisting of 1-6 bonds, obtained by condensation or rearrangement of glucose or one or more other sugars, wherein said hydrolysis is by a saccharifying enzyme selected from the group consisting of amyloglucosidase and beta-amylase to provide a hydrolysate, which is subsequently hydrogenated,
   the balance for 100% consisting of hydrogenated oligo- and polysaccharides.

2. The composition according to claim 1 wherein the concentration of said polysaccharides which are not hydrolyzed by amyloglucosidase in an F test is 1.5 to 30% by weight.

3. The composition according to claim 1 wherein the concentration of said polysaccharides which are not hydrolyzed by amyloglucosidase in an F test is 3 to 26.5% by weight.

4. The composition according to claim 1 comprising, the concentrations being expressed by weight relative to the dry matter of the composition:
   0.1 to 75% of hydrogenated monosaccharides,
   0.2 to 94% of hydrogenated disaccharides,
   22 to 94% of hydrogenated mono- and disaccharides,
   1 to 40% of said polysaccharides which are not hydrolyzed by amyloglucosidase in an F test,
   the balance for 100% consisting of hydrogenated oligo- and polysaccharides.

5. The composition according to claim 4 wherein the concentration of said polysaccharides which are not hydrolyzed by amyloglucosidase in an F test is 1.5 to 30% by weight.

6. The composition according to claim 4 wherein the concentration of said polysaccharides which are not hydrolyzed by amyloglucosidase in an F test is 3 to 26.5% by weight.

7. The composition according to claim 1 comprising, the concentrations being expressed by weight relative to the dry matter of the composition:
   0.1 to 70% of hydrogenated monosaccharides,
   0.3 to 90% of hydrogenated disaccharides,
   35 to 90% of hydrogenated mono- and disaccharides,
   1 to 40% of said polysaccharides which are not hydrolyzed by amyloglucosidase in an F test,
   the balance for 100% consisting of hydrogenated oligo- and polysaccharides.

8. The composition according to claim 7 wherein the concentration of said polysaccharides which are not hydrolyzed by amyloglucosidase in an F test is 1.5 to 30% by weight.

9. The composition according to claim 7 wherein the concentration of said polysaccharides which are not hydrolyzed by amyloglucosidase in an F test is 3 to 26.5% by weight.

10. The composition according to claim 1, wherein the hydrogenated monosaccharides are selected from the group consisting of sorbitol, mannitol, galactitol, xylitol, threitol, arabitol and erythritol.

11. The composition according to claim 1, wherein the hydrogenated disaccharides are selected from the group consisting of maltitol, hydrogenated maltulose, hydrogenated isomaltulose, isomaltitol, lactitol, and hydrogenated inulobiose.

12. The composition according to claim 1, wherein the hydrogenated oligosaccharides and polysaccharides are selected from the group consisting of maltotriitol, maltotetraitol, inulotriitol, cellobiitol, cellotriitol, xylibiitol, xylotriitol and hydrogenated oligosaccharides and polysaccharides obtained by hydrolysis of starch, cellulose, xylans or fructans.

13. The composition according to claim 1 which is not cariogenic according to a B test.

14. The composition according to claim 1, wherein the conditions for the enzymatic treatment of dextrin or polyglucose are selected such that the DE of the hydrolysate obtained at the end of this treatment is between 5 and 80.

15. The composition according to claim 1, wherein the conditions for the enzymatic treatment of dextrin or polyglucose are selected such that the DE of the hydrolysate obtained at the end of this treatment is between 10 and 65.

16. A composition of hydrogenated saccharides comprising, the concentration being expressed by weight relative to the dry matter of the composition:
   0.1 to 65% of hydrogenated monosaccharides,
   10 to 96% of hydrogenated disaccharides,
   1 to 30% of polysaccharides which can be precipitated in ethanol and which are not hydrolyzed by amyloglucosidase in an A test said polysaccharides being obtained by enzymatic hydrolysis of dextrin or polyglucose, said polyglucose predominantly consisting of 1–6 bonds, obtained by condensation or rearrangement of glucose or one or more other sugars, wherein said hydrolysis is by a saccharifying enzyme selected from the group consisting of amyloglucosidase and beta-amylase to provide a hydrolysate which is subsequently hydrogenated,
   the balance for 100% consisting of hydrogenated oligosaccharides or polysaccharides.

17. The composition according to claim 16, wherein the concentration of said polysaccharides which can be precipitated in ethanol and which are not hydrolyzed by amyloglucosidase in an A test is 1.5 to 25% by weight.

18. The composition according to claim 16, wherein the concentration of said polysaccharides which can be precipitated in ethanol and which are not hydrolyzed by amyloglucosidase in an A test is 2 to 15% by weight.

19. The composition according to claim 16 comprising, the concentration being expressed by weight relative to the dry matter of the composition:
   0.1 to 60% of hydrogenated monosaccharides,
   15 to 94% of hydrogenated disaccharides,
   1 to 30% of said polysaccharides which can be precipitated in ethanol and which are not hydrolyzed by amyloglucosidase in an A test,
   the balance for 100% consisting of hydrogenated oligosaccharides or polysaccharides.

20. The composition according to claim 19, wherein the concentration of said polysaccharides which can be precipitated in ethanol and which are not hydrolyzed by amyloglucosidase in an A test is 1.5 to 25% by weight.

21. The composition according to claim 19, wherein the concentration of said polysaccharides which can be precipitated in ethanol and which are not hydrolyzed by amyloglucosidase in an A test is 2 to 15% by weight.

22. The composition according to claim 16 comprising, the concentration being expressed by weight relative to the dry matter of the composition:
   0.1 to 55% of hydrogenated monosaccharides,
   15 to 90% of hydrogenated disaccharides,
   1 to 30% of said polysaccharides which can be precipitated in ethanol and which are not hydrolyzed by amyloglucosidase in an A test,
   the balance for 100% consisting of hydrogenated oligosaccharides or polysaccharides.

23. The composition according to claim 22, wherein the concentration of said polysaccharides which can be precipitated in ethanol and which are not hydrolyzed by amyloglucosidase in an A test is 1.5 to 25% by weight.

24. The composition according to claim 22, wherein the concentration of said polysaccharides which can be precipitated in ethanol and which are not hydrolyzed by amyloglucosidase in an A test is 2 to 15% by weight.

25. A process for preparing a composition according to claim 1, comprising the steps of:
   subjecting at least one dextrin or one polyglucose, said polyglucose predominantly consisting of 1–6 bonds, obtained by condensation or rearrangement of glucose or one or more other sugars, other to an enzymatic treatment by at least one saccharifying enzyme selected from the group consisting of amyloglucosidase and beta-amylase under conditions sufficient to obtain an hydrolysate having a DE between 5 to 80,
   adding to this hydrolysate, monosaccharides, disaccharides or oligosaccharides and polysaccharides, to obtain a mixture
   and hydrogenating the mixture to obtain a composition consisting essentially of
   0.1 to 80% of hydrogenated monosaccharides,
   0.1 to 96% of hydrogenated disaccharides,
   11 to 96% of hydrogenated mono- and disaccharides, 1 to 40% of polysaccharides which are not hydrolyzed by amyloglucosidase in an F test, the concentrations being expressed by weight relative to dry matter of the composition.

26. The process according to claim 25 which further comprises before hydrogenation a treatment using an alphaamylase.

27. The process according to claim 25 which further comprises before hydrogenation a treatment using an enzyme which hydrolyses the 1-6 bonds of amylopectin.

28. A process for preparing a composition according to claim 1, comprising the steps of:

subjecting at least one dextrin or one polyglucose, said polyglucose predominantly consisting of 1-6 bonds, obtained by condensation or rearrangement of glucose or one or more other sugars, to an enzymatic treatment by at least one saccharifying enzyme selected from the group consisting of amyloglucosidase and beta-amylase under conditions sufficient to obtain an hydrolysate having a DE between 5 to 80, hydrogenating the hydrolysate, adding to this hydrogenated hydrolysate, hydrogenated monosaccharides, disaccharides, oligosaccharides and polysaccharides, to obtain a composition consisting essentially of 0.1 to 80% of hydrogenated monosaccharides, 0.1 to 96% of hydrogenated disaccharides, 11 to 96% of hydrogenated mono- and disaccharides, 1 to 40% of polysaccharides which are not hydrolyzed by amyloglucosidase in an F test, the concentrations being expressed by weight relative to dry matter of the composition.

* * * * *